United States Patent
Maaskamp et al.

(10) Patent No.: US 12,144,948 B2
(45) Date of Patent: Nov. 19, 2024

(54) FLOW DIRECTING MEDICINAL APPLICATOR

(71) Applicant: Surgin, Inc., Scottsdale, AZ (US)

(72) Inventors: Ryan Maaskamp, Scottsdale, AZ (US); Armand Maaskamp, Scottsdale, AZ (US); Dan Thompson, Irvine, CA (US)

(73) Assignee: Medicele LLC, Scottsdale, AZ (US)

( * ) Notice: Subject to any disclaimer, the term of this patent is extended or adjusted under 35 U.S.C. 154(b) by 0 days.

(21) Appl. No.: 18/679,544

(22) Filed: May 31, 2024

(65) Prior Publication Data

US 2024/0316323 A1  Sep. 26, 2024

Related U.S. Application Data

(63) Continuation of application No. 17/895,360, filed on Aug. 25, 2022, now Pat. No. 12,023,460.

(51) Int. Cl.
*A61M 31/00* (2006.01)

(52) U.S. Cl.
CPC ..... *A61M 31/00* (2013.01); *A61M 2210/1067* (2013.01); *A61M 2210/1475* (2013.01)

(58) Field of Classification Search
CPC .. A61M 31/00; A61M 31/002; A61M 35/003; A61M 35/00; A61M 2210/1475; A61M 2210/1067
See application file for complete search history.

(56) References Cited

U.S. PATENT DOCUMENTS

| | | | |
|---|---|---|---|
| 3,667,461 A | 6/1972 | Zamarra |
| 3,894,539 A | 7/1975 | Tallent |
| 5,695,481 A | 12/1997 | Heinzelman et al. |
| 7,090,654 B2 | 8/2006 | Lotito et al. |
| 7,125,394 B2 | 10/2006 | Berman et al. |
| 7,322,953 B2 | 1/2008 | Redinger |
| 7,465,295 B2 | 12/2008 | Bergeron et al. |
| 8,092,415 B2 | 1/2012 | Moehle et al. |
| 9,132,262 B2 | 9/2015 | Berman et al. |
| 2005/0010174 A1 | 1/2005 | Berman |
| 2005/0054996 A1 | 3/2005 | Gregory |

*Primary Examiner* — Scott J Medway
(74) *Attorney, Agent, or Firm* — Kenneth Altshuler

(57) ABSTRACT

Certain embodiments of a medicinal applicator can comprise a base, a medicinal cream receiving port in the base, and a shaft with a shaft axis that is defined extending down the center of the shaft from the base and terminating at an applicator tip. There is at least one longitudinal outlet port located along a portion of the shaft. A medicinal cream passageway is in communication with the medicinal cream receiving port and the longitudinal outlet port via a funneled chamber. The medicinal cream passageway exits into the funneled chamber partway along the length of the longitudinal outlet port via a passageway exit port. A stop plate that extends essentially radially from the base delineates the base from the shaft.

20 Claims, 12 Drawing Sheets

SECTION D-D

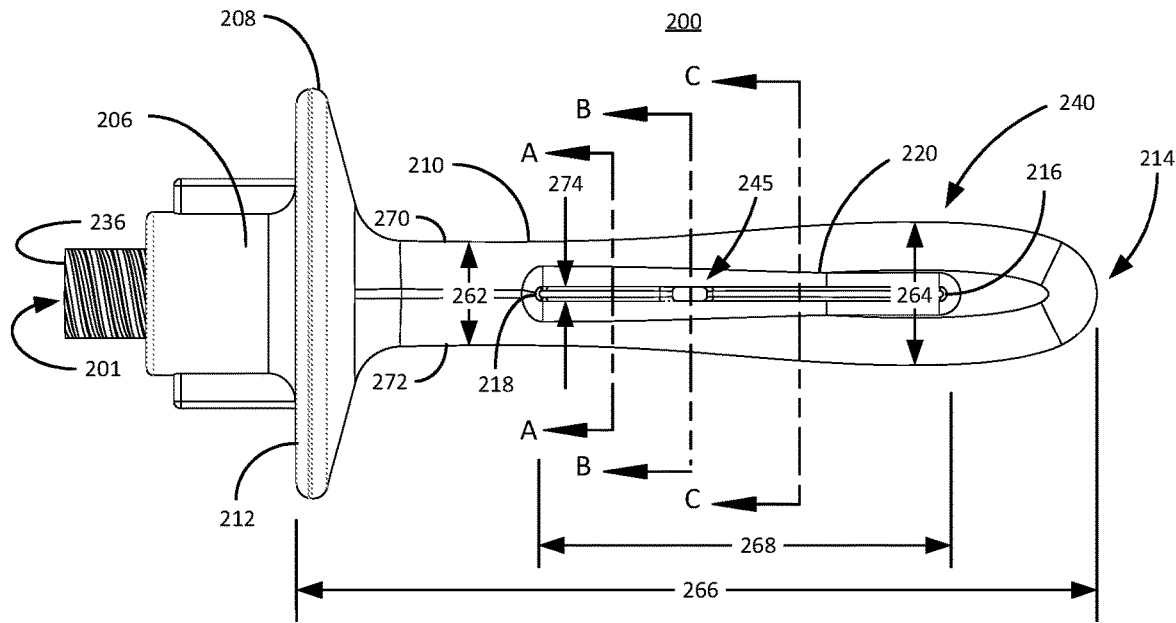
FIG. 4A
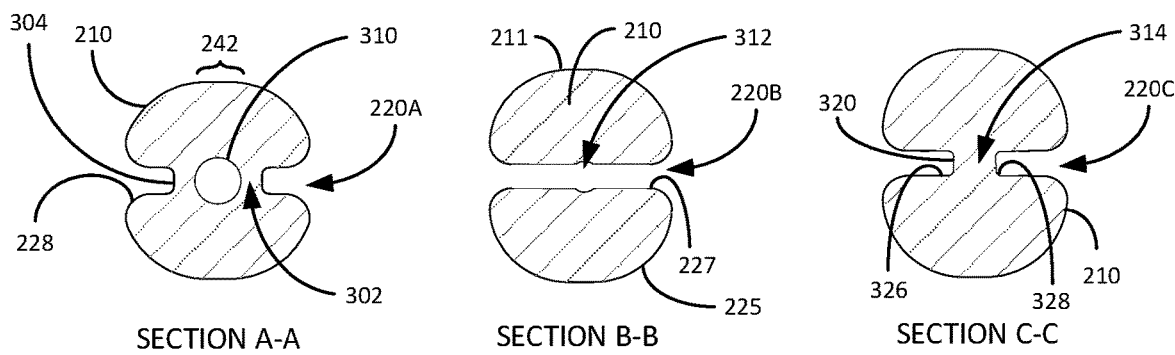
FIG. 4B  FIG. 4C  FIG. 4D

FLOW DIRECTING MEDICINAL APPLICATOR

CROSS-REFERENCE TO RELATED APPLICATIONS

This continuation application which claims priority to and the benefit of U.S. patent application Ser. No. 17/895,360 entitled: FLOW DIRECTING MEDICINAL APPLICATOR, filed on Aug. 25, 2022.

FIELD OF THE INVENTION

The present embodiments are generally directed to a medicinal dispenser probe for uniformly spreading a coat of medicinal cream within the contours of an anal or vaginal canal.

DESCRIPTION OF RELATED ART

Certain medical ailments afflict regions of human anal and vaginal canals. In some instances, these medical ailments (such as infections, viral related blisters, cancers, fissures or some other pathological pain or disease) are treatable with a medicinal cream when applied to the surface tissue of the anal and/or vaginal canal. Presently, such medicinal creams are often applied manually in the anal or vaginal canal by spreading the cream on the canal surface via a finger. One problem with using a finger to spread the medicinal cream is that it often requires the help of a second person because it is difficult to auto apply (i.e., self-apply) the medicinal cream. Accordingly, applicators for dispensing a medicinal cream to these canals exist so that people can independently apply (auto apply) medicinal cream to themselves (their anal or vaginal canal) without the help of a second person.

FIG. 1A, in view of FIG. 1B, illustratively depicts a line drawing of a prior art applicator for auto application of a medicinal substance in an anal canal. As shown, the applicator 100 possesses a handle 106, a shaft 110 that extends from the handle 106 and terminates in a rounded dome 104 at the distal end of the applicator 100. As shown, the rounded dome 104 has a diameter that never exceeds the diameter of the shaft 110 in order to facilitate easy insertion in a human anus. The proximal end 102 of the applicator 100 is adapted to receive a medicinal cream (or other viscous material/s) by way of an aperture 101. There is an unobstructed pathway 121 (see FIG. 1B) between the aperture 101 and two slots 120, the two slots are axially located along the length of the shaft 110. The applicator 100 is universal to any natural opening of the anatomy of a human body including vaginal openings and anal openings. Accordingly, the applicator 100 is nonspecific to any particular anatomy of any specific opening of a human body.

In practice, the applicator 100 can be gripped via the handle 106, inserted through the anus and into the anal canal whereby medicinal cream can be forced through the aperture 101 and out through the slots 120. While the medicinal cream is being pushed out of the slots when the shaft is deployed in the human anal canal, a person can rotate the shaft 110 by way of turning the handle 106 to coat the surface of the anal canal. Because the applicator 100 is not specific to any particular anatomy of any specific opening of a human body, the cross-section of the shaft 110 maps to a circular profile or shape 161.

FIG. 1B is a prior art line drawing that illustratively depicts the flow of medicinal cream 130 that goes into the unobstructed pathway 121 via the aperture 101 and out through the two slots 120. The unobstructed pathway 121 exits into the slots 120 at each of the slot's proximal ends 125.

Hence, the applicator 100 provides the benefit of auto application of medicinal cream 130. However, the applicator 100 is deficient in applying medicinal cream 130 with sufficient coverage to the entire surface of the anal canal. Accordingly, it is to improvements to the present subject matter that the claimed invention is generally directed.

SUMMARY OF THE INVENTION

The present embodiments are generally directed to a medicinal applicator for auto application to improve uniformly spreading a coat of medicinal cream within the contours of an anal or vaginal canal.

Certain embodiments contemplate a medicinal applicator that can comprise a base with a medicinal cream inlet port in the base and a shaft residing along a shaft axis that extends from the base to an anal applicator cap. A medicinal cream passageway (which includes a luer taper, a central passageway a passageway reducer and a passageway exit port) extends inside of the shaft along the shaft axis from the medicinal cream inlet port to a flow directing channel, which in certain embodiments facilitate a lower required pressure to push medicinal cream through the flow directing channel. The medicinal cream passageway joins, or is otherwise in communications with, the flow directing channel at a passageway exit port inside of the shaft. The flow directing channel outwardly funnels from the passageway exit port to a longitudinal outlet slot. The longitudinal outlet slot is partially defined by a slot length that is longitudinally in plane with the shaft axis. In other words, a plane can bisect the longitudinal outlet slot and pass through the shaft axis. The longitudinal outlet slot penetrates through an outer shaft surface of the shaft, thereby forming communication with an outside environment interfacing the shaft outer surface of the shaft and the medicinal cream inlet port. In this way, medicinal cream can enter through the medicinal cream inlet port and go through the shaft and out through the longitudinal outlet slot. The passageway exit port is located between 10% and 90% of the slot length from a slot proximal end.

In yet another embodiment of the present inventions, an applicator for medicinal cream can comprise a rectal/vaginal shaft separated from a handle via a stop plate. A shaft axis is defined extending through the center of the handle to a shaft cap to where the shaft terminates distally. A longitudinal outlet slot is at least partially defined by a slot length residing lengthwise in the shaft between the stop plate and the shaft cap. A passageway extends inside of the shaft from a receiving port in the handle to a passageway exit port inside of the shaft. The passageway exit port is located between 10% of a proximal end of the slot length and 90% of the slot length. The receiving port is in communication with the longitudinal outlet slot via the passageway exit port.

Still another embodiment envisions a rectal/vaginal medicinal applicator that can comprise a shaft that extends from a base to a distal end via a stop plate. There are at least two longitudinal parallel outlet slots each outlet slot defining a slot length residing lengthwise along the shaft between the stop plate and the distal end. A passageway inside of the applicator communicatively links an inlet port in the base to a passageway exit port inside of the shaft. Communicatively links means that the inlet port is in communication with the passageway outlet port so that medicinal cream can flow without obstruction there through. At least two flow directing channels, wherein each flow directing channel funnels outwardly from the passageway exit port to a corresponding one of the longitudinal outlet slots. The passageway exit port is located between 10% and 90% of the slot length. The inlet port is in communication with the outlet slots via the passageway and the flow directing channels.

BRIEF DESCRIPTION OF THE DRAWINGS

FIG. 4A is the line drawing of the medicinal applicator embodiment depicted in FIG. 3A with cut-lines and example dimensions;

FIG. 4B is a line drawing of the shaft cross section A-A at the cut-line A-A of FIG. 4A;

FIG. 4C is a line drawing of the shaft cross-section B-B at the cut-line B-B of FIG. 4A;

FIG. 4D is a line drawing of the shaft cross-section C-C at the cut-line C-C of FIG. 4A;

DETAILED DESCRIPTION

Figure 1A:
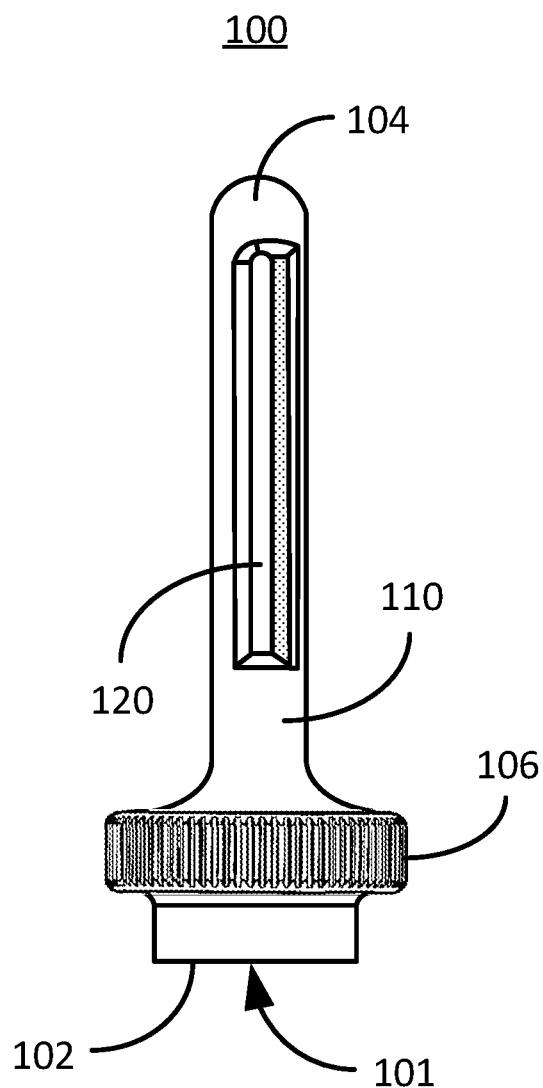
FIG. 1A illustratively depicts a line drawing of a prior art applicator for auto application of a medicinal substance in an anal canal.
Figure 1B:
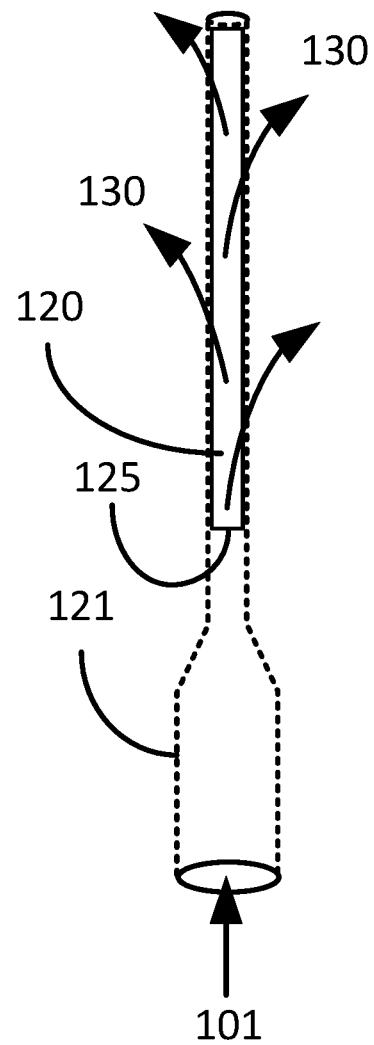
FIG. 1B illustratively depicts a line drawing of the unobstructed pathway system of the prior art applicator.

Initially, this disclosure is by way of example only, not by limitation. Thus, although the instrumentalities described herein are for the convenience of explanation, shown and described with respect to exemplary embodiments, it will be appreciated that the principles herein may be applied equally in other similar configurations involving uses of anal probes for use in spreading medicinal cream. The phrases "in one embodiment", "according to one embodiment", and the like, generally mean the particular feature, structure, or characteristic following the phrase, is included in at least one embodiment of the present invention and may be included in more than one embodiment of the present invention. Importantly, such phases do not necessarily refer to the same embodiment. If the specification states a component or feature "may", "can", "could", or "might" be included or have a characteristic, that particular component or feature is not required to be included or have the characteristic. As used herein, the terms "having", "have", "including" and "include" are considered open language and are synonymous with the term "comprising". Furthermore, as used herein, the term "essentially" is meant to stress that a characteristic of something is to be interpreted within acceptable tolerance margins known to those skilled in the art in keeping with typical normal world tolerance, which is analogous with "more or less." For example, essentially flat, essentially straight, essentially on time, etc. all indicate that these characteristics are not capable of being perfect within the sense of their limits. Accordingly, if there is no specific +/− value assigned to "essentially", then assume essentially means to be within +/−2.5% of exact. The term "connected to" as used herein is to be interpreted as a first element physically linked or attached to a second element and not as a "means for attaching" as in a "means plus function". In fact, unless a term expressly uses "means for" followed by the gerund form of a verb, that term shall not be interpreted under 35 U.S.C. § 112(f). In what follows, similar or identical structures may be identified using identical callouts.

Described herein includes embodiments of an anal or vaginal medicinal applicator that, in certain configurations, can comprise a base, a medicinal cream receiving port in the base, and a shaft with a shaft axis that is defined extending down the center of the shaft from the base and terminating at an applicator tip. There is at least one longitudinal outlet port located along a portion of the shaft. A medicinal cream passageway is in communication with the medicinal cream receiving port and the longitudinal outlet port via a funneled chamber, which makes up a significant part of the flow director. In certain embodiments, the flow director facilitate a lower required pressure to push medicinal cream through the flow directing channel. The medicinal cream passageway exits into the funneled chamber partway along the length of the longitudinal outlet port via a passageway exit port. The funneled chamber comprises ramps (hence the funnel shape) that provides uniform coverage of medicinal cream over the shaft and on to an anal/vaginal canal when dispensed through the at least one longitudinal outlet port. A stop plate that extends essentially radially from the base delineates the base from the shaft to prevent the handle from entering the anus or vagina.

Figure 2A:
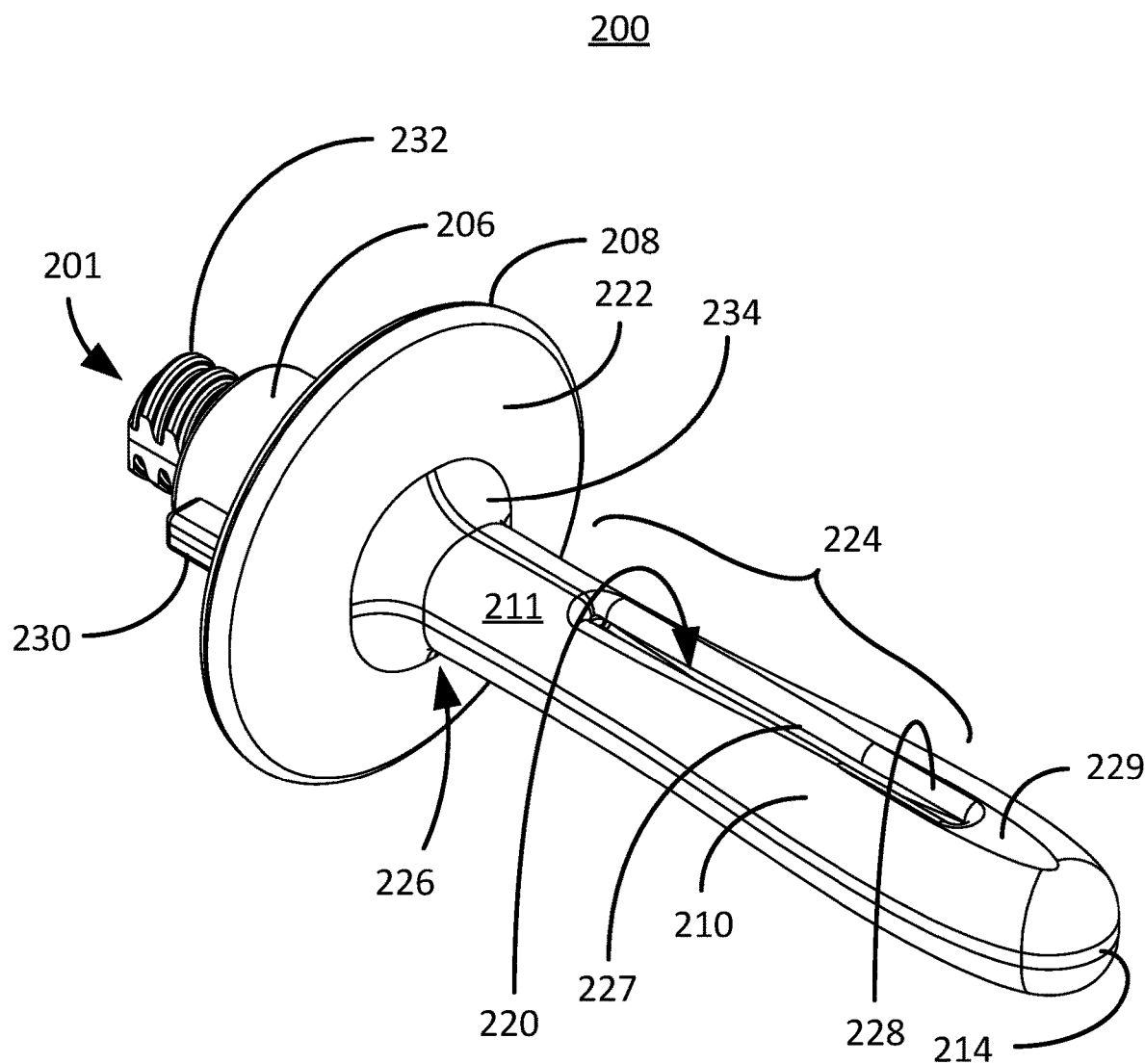
FIG. 2A illustratively depicts a front-view isometric line drawing of the medicinal applicator embodiment.
Figure 2B:
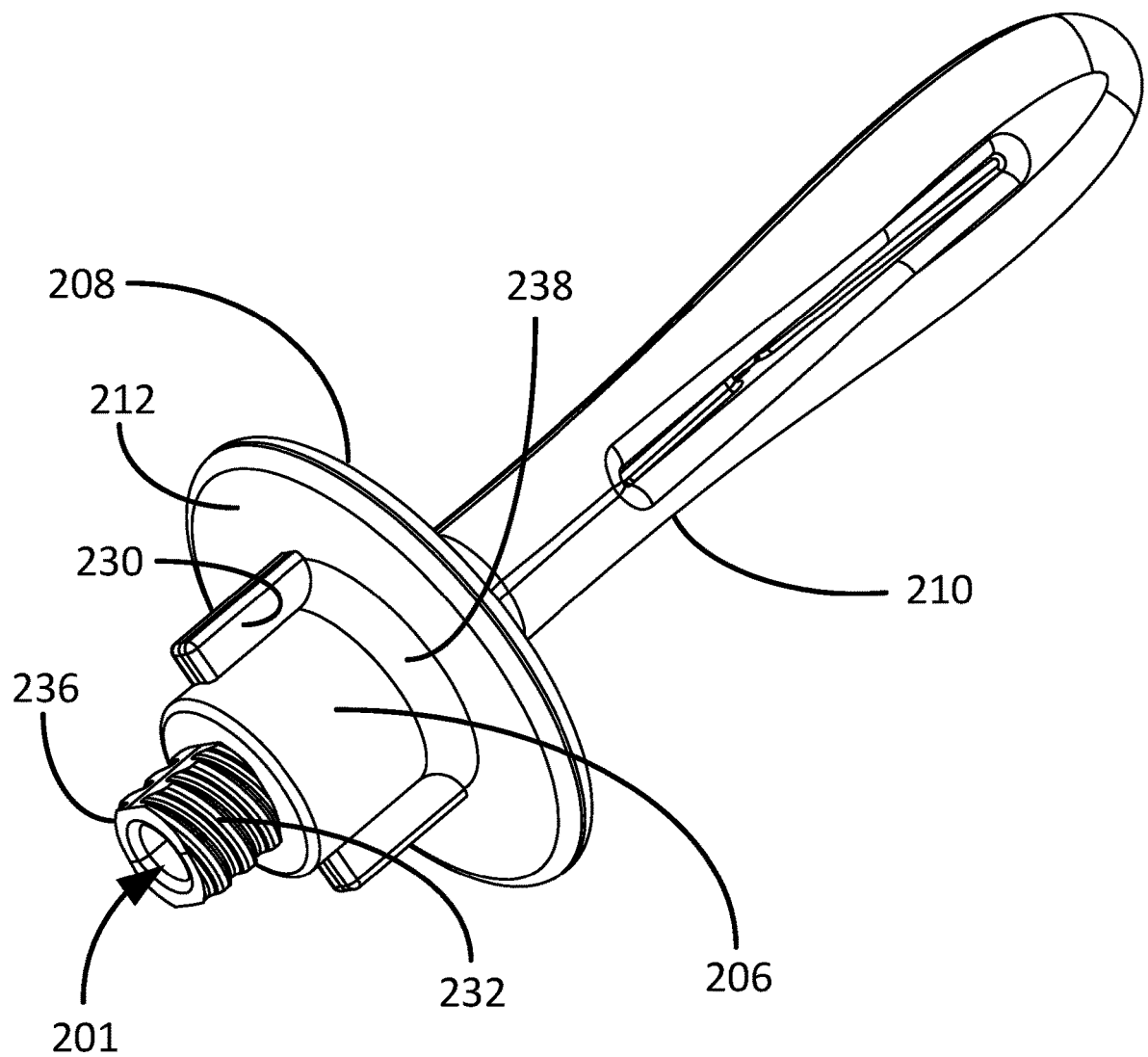
FIG. 2B illustratively depicts a rear-view isometric line drawing of the medicinal applicator embodiment.

FIGS. 2A and 2B are front-view and rear-view line drawings of an anal medicinal applicator embodiment 200 consistent with embodiments of the present invention. FIG. 2A illustratively depicts a front-view isometric line drawing of the medicinal applicator embodiment 200. The medicinal applicator 200 generally comprises a handle 206 that is separated from a medicinal applicator shaft 210 by a stop plate 208. The handle 206 can be gripped by a human hand to maneuver the medicinal applicator shaft, or simply "shaft" 210 into, around, and out from a human anal cavity or vaginal cavity. The stop plate contact surface 222 is configured to rest up against a person's anus or vaginal opening under normal use with the handle 206 and syringe 350 (of FIG. 7B) permanently outside of the human body. In the present embodiment, the stop plate 208 is circular with contact surface 222 being tapered. The contact surface 222 tapers into the shaft proximal region 226 via a stop plate radius 234, which may or may not be a constant radial arc.

The distal end 214 of the shaft 210 is dome-shaped for easy insertion into an anus 820 or vagina (not shown) as far as the stop plate 208 will allow. The longitudinal outlet slot 220 is defined by a slot length 224 slot width 274 (of FIG. 3A), which are defined a location in the shaft 210 at the slot-round interface 227 where the corresponding slot round 228 starts. The outlet slot 220 is located along the length of the shaft 210 between the shaft proximal end 226 and the dome cap 215. The distal point of the dome cap 215 is the distal end of the anal medicinal applicator 200. In the present embodiment, the longitudinal slot 220 transitions to the outer shaft surface 211 by way of a slot round 228 (which is a fillet), however other shapes, such as a chamfer for example can be equally used without departing from the scope and spirit of the present invention.

FIG. 2B illustratively depicts a rear-view isometric line drawing of the medicinal applicator embodiment 200. As shown, the handle 206 comprises diametrically opposed protruding ribs 230 that can be used as 'grips' to twist the shaft 210 either clockwise or counterclockwise when inserted in a vaginal cavity or anal cavity (simply considered a cavity). The protruding ribs 230 extend along most of the handle 206 from approximately where the threaded post 232 meets the handle 206 to the stop plate 208, as shown. The treaded post 232 is configured to screw into a threaded channel at the end of a syringe or tube. For reference, the stop-plate-handle surface 212 of the stop plate 208 meets the handle 206 handle surface by way of a handle-to-stop-plate radius 238.

Figure 3A:
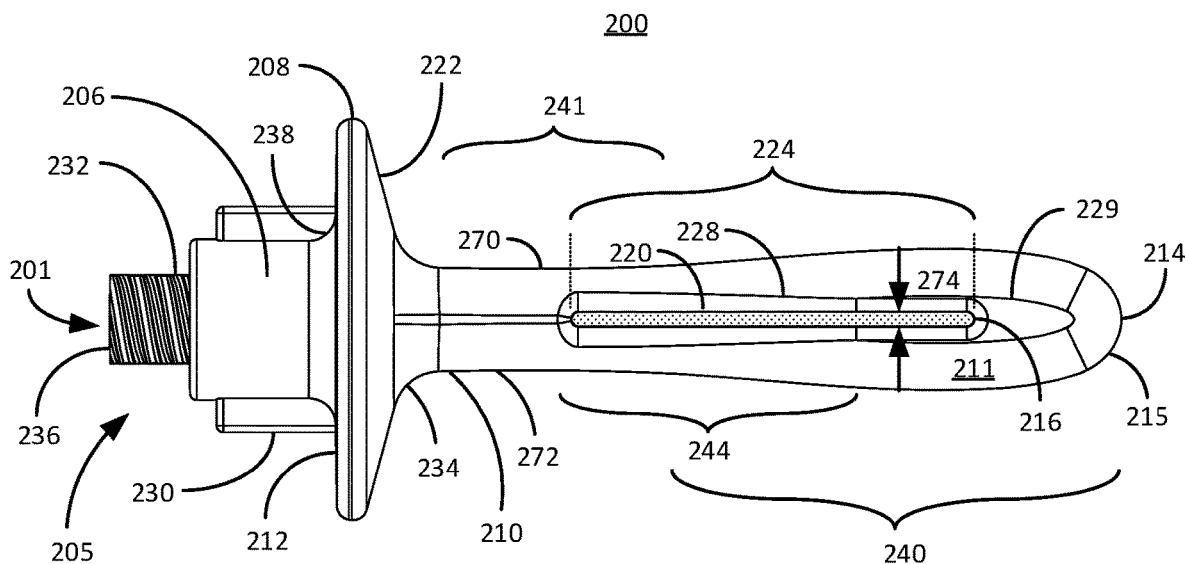
FIG. 3A is a side view line drawing of the medicinal applicator embodiment.

FIG. 3A is a side view line drawing of the medicinal applicator embodiment 200. As described in connection with FIGS. 2A and 2B, the medicinal applicator 200 comprises a base 205, which collectively includes the threaded post 232, the shaft 210 that is separated from the base 205 by way of the stop plate 208. The base 205 comprises an inlet port 201 at the applicator proximal end 236. The handle 206 further depicts the opposing pair of protruding handle ribs 230. In the present embodiment, the handle 206 blends into the stop-plate-to-handle surface 212 by way of a stop-plate-to-handle radius 238. Certain embodiments envision that instead of the medicinal applicator 200 having a threaded post 232, the base 205 comprises a female threaded receiving port (not shown) that mates with an external male threaded post (not shown). The external male threaded post is envisioned to be at the dispensing end of a tube or syringe of medicinal cream, or some other kind of medicinal cream dispensing apparatus.

With continued reference to the medicinal applicator embodiment 200, the shaft 210 is paddle shaped having essentially a uniform proximal shaft region 241 (from the leading edge 270 to the trailing edge 272) at the shaft proximal end 226 that transitions into a paddle shaped region 240 that terminates at the shaft distal end 214. For added comfort to the patient using the medicinal applicator 200, the stop plate contact surface 222 smoothly transitions to the shaft 210 with a stop plate radius 234. As further shown, a longitudinal outlet slot 220 (shown with a pattern fill) extends in length 224 from the proximal shaft region 241 and into the paddle region 242. The longitudinal outlet slot 220 is an aperture in the shaft 210 where medicinal cream (not shown) exits the shaft 210. The paddle 240 actively spreads/smears the medicinal cream that exits through the outlet slot 220 on the contact region in a person's rectum, colon or vaginal cavity, for example. The outlet slot 220 has a constant slot width 274 across the slot length 224 with rounded ends to improve the flow of medicinal cream that passes over the slot rounds 228. The slot rounds 228 are rounded corners that blend into the shaft outer surface 211. In the present embodiment, there is a distal recess 229 at the distal end 216 of the outer slot 220 to help the medicinal cream flow towards the shaft distal end 214 when the medicinal cream is being ejected through the outer slot 220.

Figure 3B:
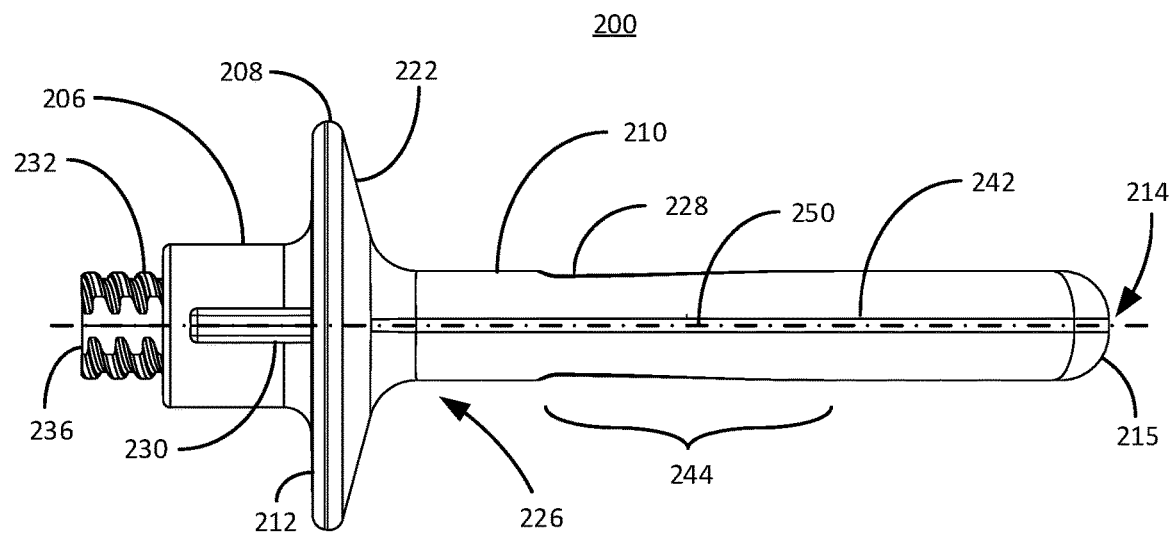
FIG. 3B is a top view line drawing of the medicinal applicator.

FIG. 3B is a top view line drawing of the medicinal applicator 200. A central axis 250 passes through the center of the medicinal applicator 200, i.e., axially through the medicinal applicator 200, from the applicator proximal end 236 to the applicator distal end 214. Likewise, from the perspective of the medicinal applicator 200 of FIG. 3A, though expressly depicted, the central axis 250 passes through the center of the base 205, the stop plate 208 and the longitudinal outlet slot 220. With continued reference to FIG. 3B, the handle 206, the threaded post 232 and the protruding handle ribs 230 all extend from the stop-plate-to-handle surface 212 to the applicator proximal end 236. On the other side of the stop plate 210, the shaft 210 extends from the stop plate contact surface 222 to the applicator distal end 214. In this embodiment, the shaft 210 comprises a shaft flat 242 that is located along the top surface of the shaft 210 from the shaft proximal end 226 to the shaft distal end 214. Though not shown in this figure, the shaft embodiment 210 comprises a shaft flat 242 on the opposing side (bottom) of the shaft 210. Moreover, in this medicinal applicator embodiment 200, the slot round 228 tapers at a slot fillet taper region 244, which narrows the width of the shaft 210 (from an otherwise constant width) towards the proximal shaft end 226 of the longitudinal outlet slot 220. The slot fillet taper region 244 is envisioned to improve the flow of medicinal cream at a rectal or vaginally wall near to the stop plate 208.

FIG. 4A is the line drawing of the medicinal applicator embodiment 200 depicted in FIG. 3A with cut-lines and example dimensions. In one embodiment of the medicinal applicator 200, the length 266 from the stop-plate-to-handle surface 212 to the distal end 214 is approximately 4.6 inches. The slot length 268 of the longitudinal outlet slot 220 (not including the slot round 228) is approximately 2.33 inches. The proximal shaft region distance 262 from the leading edge 270 to the trailing edge 272 in the proximal shaft region 241 (see FIG. 3A) is approximately 0.6 inches, and the maximum paddle distance 264 from the leading edge 270 to the trailing edge 272 in the paddle region 240 is approximately 0.83 inches. The longitudinal slot width 274, along most of the slot length 224, is approximately 0.09 inches. The outlet slot 220 is in communication with the inlet port 201 via a chamber funnel inlet 245. The chamber funnel inlet 245 being at about 35% of the slot length 224 from the slot proximal end 218.

FIG. 4B is a line drawing of the shaft cross section A-A at only the cut-line A-A of FIG. 4A, meaning that the other parts of the medicinal applicator 200 towards the proximal applicator end 236 are not shown. The shaft 210 along cut-line A-A is on the distal end of the proximal shaft region 241 (immediately to the left of the paddle region 240), which is essentially the narrowest part of the shaft 210 defined between the leading edge 270 in the trailing edge 272. As shown, the shaft cross section A-A comprises a medicinal cream tubular passageway 310, which in the present embodiment is circular. The passageway 310 is configured to carry medicinal cream that is introduced to the medicinal applicator 200 via the inlet port 201 to the longitudinal outlet slot 220. The passageway 310 is separated from the proximal longitudinal slot portion 220A by way of a passageway barrier 302 that defines a proximal slot ramp 304. For reference, a profile of the shaft flat 242 and slot round 228 are labeled.

FIG. 4C is a line drawing of the shaft cross-section B-B at only the cut-line B-B of FIG. 4A, meaning that the other parts of the medicinal applicator 200 towards the proximal applicator end 236 are not shown. The shaft cut-line B-B is in the middle of the chamber funnel inlet 245, which is immediately distal to the medicinal cream passageway exit port 246. The medicinal cream passageway exit port 246 is where the medicinal cream passageway 310 terminates inside of the shaft 210. At the shaft cross-section B-B, medicinal cream is configured to flow directly out from the shaft exit port 246 via the chamber funnel inlet 245 and out the longitudinal-slot-at-passageway-exit-port 220B. Also for reference, the slot-round interface 227 is labeled, which defines the edge of the longitudinal outlet slot 220. Though the slot-round interface 227 is at the beginning of the slot round two of the slot round 228, certain embodiments contemplate a slot facet (straight line) starting at the slot interface 227 and terminating at the outer shaft surface 211. Note that the shaft 210 is more oblong than the shaft cross-section A-A of FIG. 4B. By oblong it is meant that the cross-sectional shape of the shaft 210 at cross-section A-A is oblong shaped, which is defined herein as an object having an elongated shape such as a rounded rectangle or oval or a racetrack that is essentially a circle that has been stretched with linear sides and circular ends. As further defined herein, protrusions or features extending from an elongated shape (e.g., square, a rounded square, circle, etc., that is elongated in one dimension) do not in themselves define and oblong shape. This particular oblong shaped cross-section along the shaft 210 is rectangular shaped with rounded corners 225.

FIG. 4D is a line drawing of the shaft cross-section C-C at only the cut-line C-C of FIG. 4A, meaning that the other parts of the medicinal applicator 200 towards the proximal applicator end 236 are not shown. The shaft cut-line C-C is partway along the longitudinal outlet slot 220 towards the distal applicator end 214. There are opposing distal longitudinal slot regions 220C separated by a slot separator region 314 that increases towards the slot distal end 216. In this embodiment, the longitudinal slot regions 220C comprise a blending radius 328 between the slot ramp 320 and the chamber wall 326. Note that the shaft 210 at cut-line C-C is more oblong than the shaft cross-section B-B of FIG. 4C.

Figure 4E:
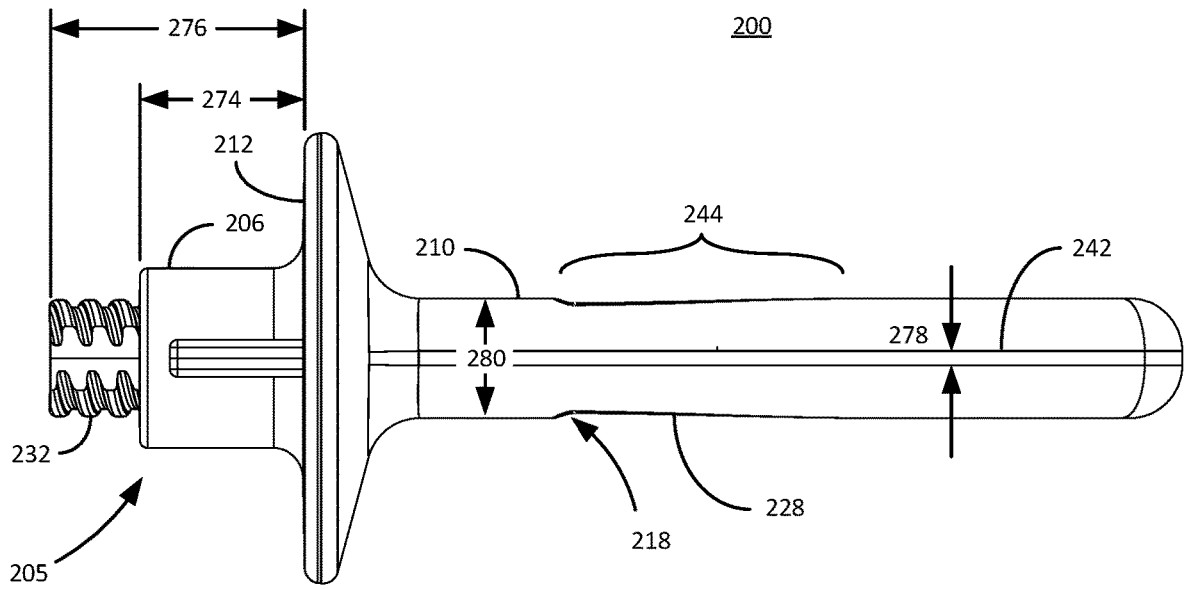
FIG. 4E is a line drawing of the medicinal applicator embodiment depicted in FIG. 3B with example dimensions.

FIG. 4E is a line drawing of the medicinal applicator embodiment 200 depicted in FIG. 3B with example dimensions. In one embodiment of the medicinal applicator 200, the base length 276 from the stop-plate-to-handle surface 212 to the distal end 214 is approximately 4.6 inches. The handle length 275 is approximately 0.87 inches. The shaft flat 242 comprises a shaft flat width 278 that is approximately 0.08 inches. The slot fillet taper 244 increasingly narrows the shaft width 280 towards the slot proximal end 218 of the longitudinal outlet slot 220.

Figure 4F:
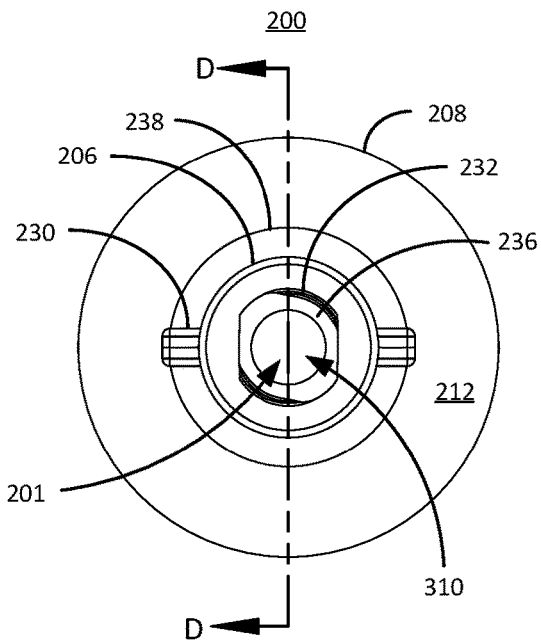
FIG. 4F is a line drawing of the medicinal applicator as viewed from the circular applicator proximal end pointing out of the page.

FIG. 4F is a line drawing of the medicinal applicator 200 as viewed from the circular applicator proximal end 236 pointing out of the page. Accordingly, the stop-plate-to-handle surface 212 of the circular stop plate 208 is also in-line with the page. It should be appreciated that the circular elements of the present embodiment may not be circular in other embodiments (e.g., the circular elements can be elliptical, angular, etc., so long as they are able to function within the scope and spirit of the present invention). As viewed from this perspective, the handle 206 blends into the stop-plate-to-handle surface 212 by way of the stop-plate-to-handle radius 238. The two opposing protruding handle ribs 230 extend outwardly from the handle 206. And, the inlet port 201 is located at the applicator proximal end 236, which defines the edge of the threaded post 232. The inlet port 201 is the opening to the medicinal cream passageway 310, which is the conduit for medicinal cream to reach the to reach the longitudinal outlet slots 220.

Figure 5A:
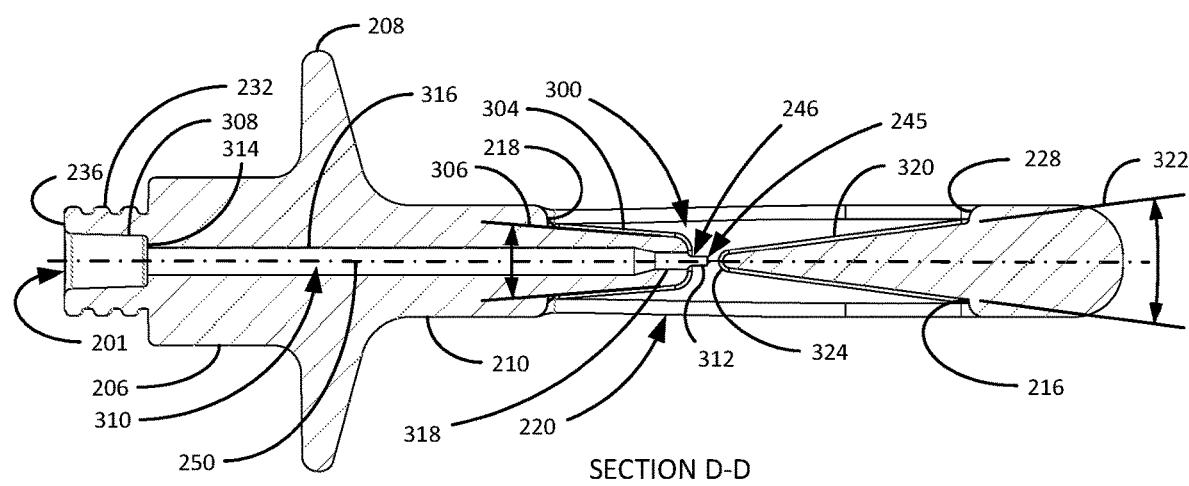
FIG. 5A is a line drawing of an embodiment of cross-section D-D of the medicinal applicator along cut-line D-D of FIG. 4F.

FIG. 5A is a line drawing of an embodiment of cross-section D-D of the medicinal applicator 200 along cut-line D-D of FIG. 4F illustrating the medicinal cream path from entry into and exit out from the medicinal applicator 200. Starting from the applicator proximal end 236, medicinal cream enters the medicinal applicator 200 via the inlet port 201 that opens into a luer taper 308 of the medicinal cream passageway 310. The luer taper 308 is in the distal base region defined by the threaded post 232, hence the luer taper 308 extends from the applicator proximal end 236 to the handle 206. The luer taper 308 slopes from a larger diameter at the inlet port 201 to a smaller diameter at the central passageway interface 314. The medicinal cream passageway 310 comprises a central passageway 316 that is essentially a constant diameter internal tube that extends along the inside of the medicinal applicator 200 through the handle 206 and stop plate 208 into a passageway reducer 318 that opens into a funneled chamber 300 via a passageway exit port 246 that is located partway along the shaft 210.

The passageway exit port 246 opens into the chamber funnel inlet 245, which is at the smallest part of the funneled chamber 300. The chamber funnel inlet 245 widens to the longitudinal outlet slots 220 as shown thereby forming the funneled chamber 300. More specifically, the funneled chamber 300 ramps to the slot proximal end 218 via the proximal slot ramp 304 and ramps to the slot distal end 216 via the distal slot ramp 320. The longitudinal outer slot 220 transitions into the outer shaft surface 211 via the slot rounds 228. In this embodiment the proximal slot ramp angle 306 is 9° from the horizontal and the distal slot ramp angle 322 is 15° from the horizontal. Other embodiments envision higher or lower ramp angles 306 and 322 than those which are depicted in the present embodiment. In this embodiment, the chamber walls 326 are parallel and are the same width apart as the slot width 274, except for the wall-to-ramp blending radius 328. Certain embodiments envision that the passageway exit port 246, the funneled chamber 300, the longitudinal outlet slots 220 and the slot rounds 228, which together essentially make up the flow directors, make it easier for an user to dispense medicinal cream 330 as compared with the prior art medicinal cream dispensers 100.

Figure 5B:
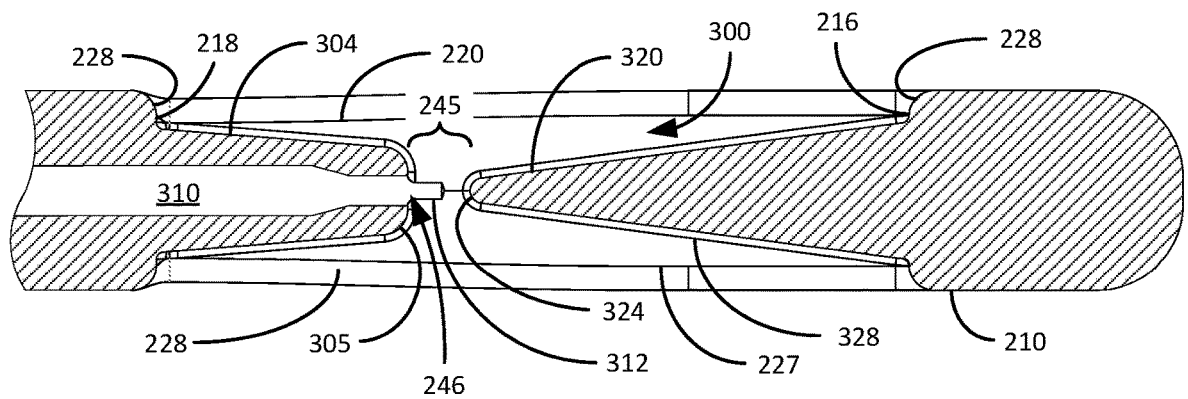
FIG. 5B is a line drawing of the funneled chamber.

FIG. 5B is a line drawing of the funneled chamber 300 with higher resolution. The crosshatched area is the cross-section of solid material (such as a polymer) comprising the shaft 210. The shaft 210 optionally be comprised of different layers of material, although that material, composite material, blended composite material, etc., without departing from the scope and spirit of the present invention. The medicinal cream passageway 310 exits into the chamber funnel inlet 245 year the passageway exit port 246. In the present embodiment, there is a passageway exit port recess 312 in the wall 326 of the funneled chamber 300. Also, as touched upon earlier, there is a blending radius 328 between the ramps 304 and 320 and the chamber walls 326. In the present embodiment, the chamber walls 326 are parallel and are essentially the same as the slot width 274. The passageway exit port 246 at approximately 30% of the slot length 268 from the slot proximal end 218. Certain other embodiments envision the passageway exit port 246 being between 10% and 90% of the slot length 268 from the slot proximal end 218. For reference, the slot-round interface 227 is labeled, which defines the longitudinal outlet slot 220. The passageway exit port 246 is an aperture that opens at a proximal ramp bend 305, which transitions into the proximal slot ramp 304, as shown. The distal ramp cone 324 opposes the passageway exit port 246. The distal ramp cone, or nose, 324 transitions into the start of the distal slot ramp 320. As shown, there are two opposing longitudinal outlet slots 220 that are mirror images. Hence, the funneled chamber 300 starts at the chamber funnel inlet 245 and angles outwardly to the longitudinal outlet slot 220 defined at the slot-round interface 227.

Figure 5C:
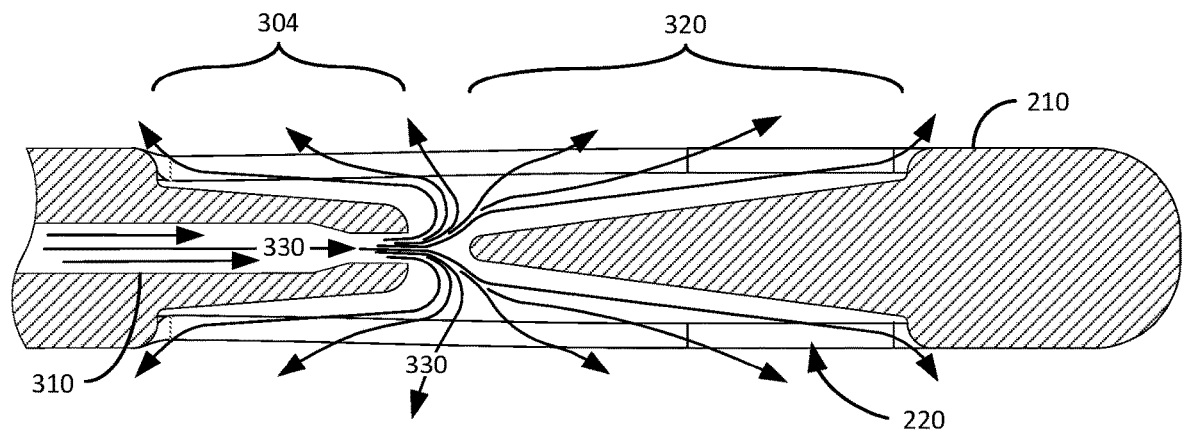
FIG. 5C is a line drawing of the cross-section of FIG. 5B with flow arrows of medicinal cream.

FIG. 5C is the cross-section of FIG. 5B but with flow arrows of medicinal cream 330 depicting how the medicinal cream 330 flows through the medicinal cream passageway 310 over the proximal slot ramp 304 and the distal slot ramp 320 as the medicinal cream 330 exits the shaft 210. The angles 306 and 322 and lengths of the respective ramps 304 and 320 improves uniformity in flow of medicinal cream 330 out from the exit slots 220.

Figure 6A:
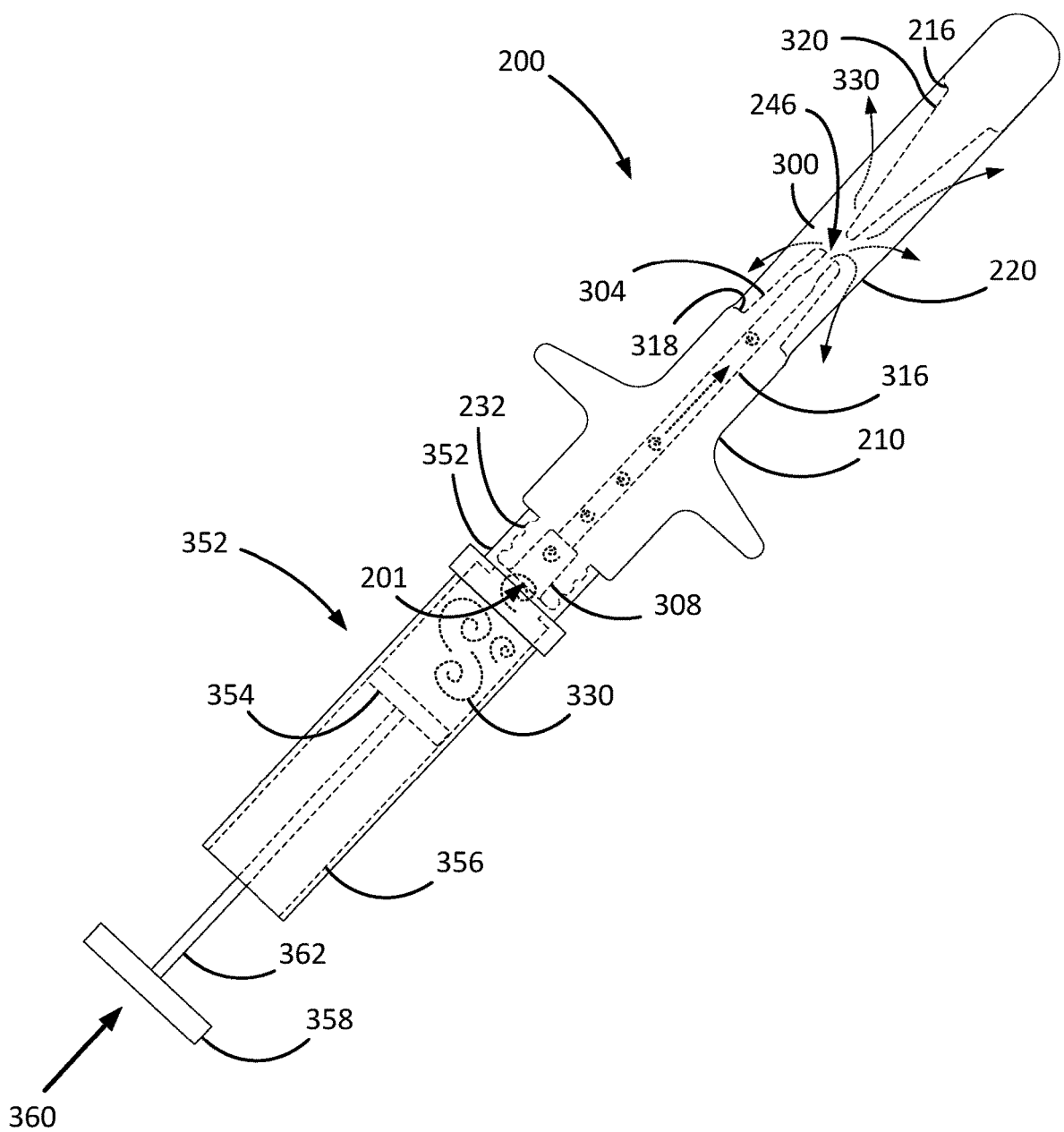
FIG. 6A illustratively depicts a line drawing of an anal medicinal applicator cooperating with a syringe consistent with embodiments of the present invention.

FIG. 6A illustratively depicts a line drawing of an anal medicinal applicator 200 cooperating with a syringe consistent with embodiments of the present invention. The anal medicinal applicator 200 is fixedly attached with a syringe 350 by way of the threaded post 232 that matingly engages threaded receiving sleeve 352. In this example, the syringe 350 is partially depressed, i.e., the plunger seal 354 is displaced partway down barrel/tube 356. In practice, a person squirting/dispensing medicinal cream 330 either into their anal canal (self-administering) or someone else's anal canal will grip the syringe barrel 356 and depress the plunger top 358 in the direction of arrow 360. By depressing the plunger top 358, the plunger piston 362 physically pushes the medicinal cream 330, via the plunger seal 354, into the medicinal applicator 200. The medicinal cream 330 is pushed into the inlet port 201 and into the luer taper 308 and down the central passageway 316 before exiting into the funneled chamber 300 via the passageway exit port 246. As depicted in FIG. 5C, the medicinal cream 330 is pushed out of the longitudinal exit slots 220 uniformly by moving down the slot distal ramp 320 towards the slot distal end 216 and the slot proximal ramp 304 towards the slot proximal end 218.

Figure 6B:
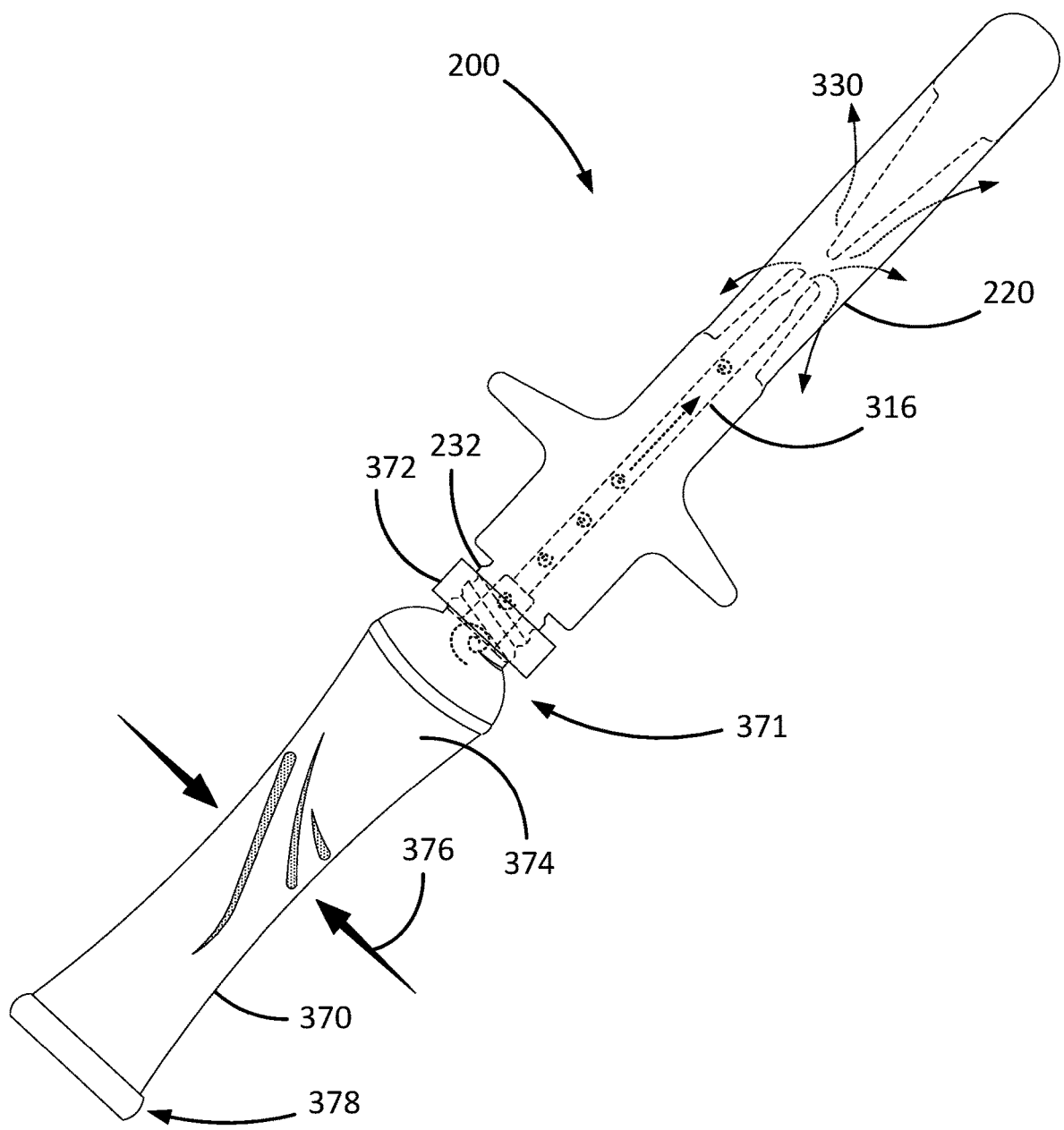
FIG. 6B illustratively depicts a line drawing of an anal medicinal applicator cooperating with a tube of medicinal cream consistent with embodiments of the present invention.

FIG. 6B illustratively depicts a line drawing of an anal medicinal applicator cooperating (attached) with a tube of medicinal cream consistent with embodiments of the present invention. As shown in the present embodiment, the medicinal applicator 200 is screwed onto a tube of medicinal cream 370. The tube of medicinal cream 370, or simply dispensing tube, is yet another embodiment of a medicinal cream dispensing apparatus. The dispensing tube 370 comprises a threaded receiving port 372, wherein the threaded post 232 is screwed into the threaded receiving port 372 to connect the dispensing tube 370 to the medicinal applicator 200. The dispensing tube 370 comprises a flexible body 374, which can be squeezed by a human hand that is gipping the dispensing tube 370 in the direction of the arrows 376. The medicinal cream 330 can be dispensed through the medicinal applicator 200 by starting at the tube free end 378 and moving towards the tube attached end 371 until the medicinal cream 330 is dispensed from the dispensing tube 370. In this way, medicinal cream 330 contained inside of the dispensing tube 370 is dispensed from the dispensing tube 370 through the central passageway 316 of the medicinal applicator 200 and out through the longitudinal outlet slots 220. Other than connecting the dispensing tube 370 to the medicinal applicator 200, the arrangement of FIG. 6B dispenses the medicinal cream 330 out from the medicinal applicator 200 in the same way as the syringe 350 does as described in FIG. 6A. Certain embodiments envision the dispensing tube 370 or syringe 350 and the medicinal applicator 200 being a single use arrangement. Other embodiments envision a single use medicinal applicator 200 and medicinal cream dispensing apparatus (e.g., 350 or 370) being connected in a manner that is not intended to be separated, such as by a mechanical latch or adhesive. In this way, when the medicinal cream 330 is no longer in the medicinal cream dispensing apparatus, the entire arrangement (medicinal applicator 200 and medicinal cream dispensing apparatus) is discarded.

Figure 7A:
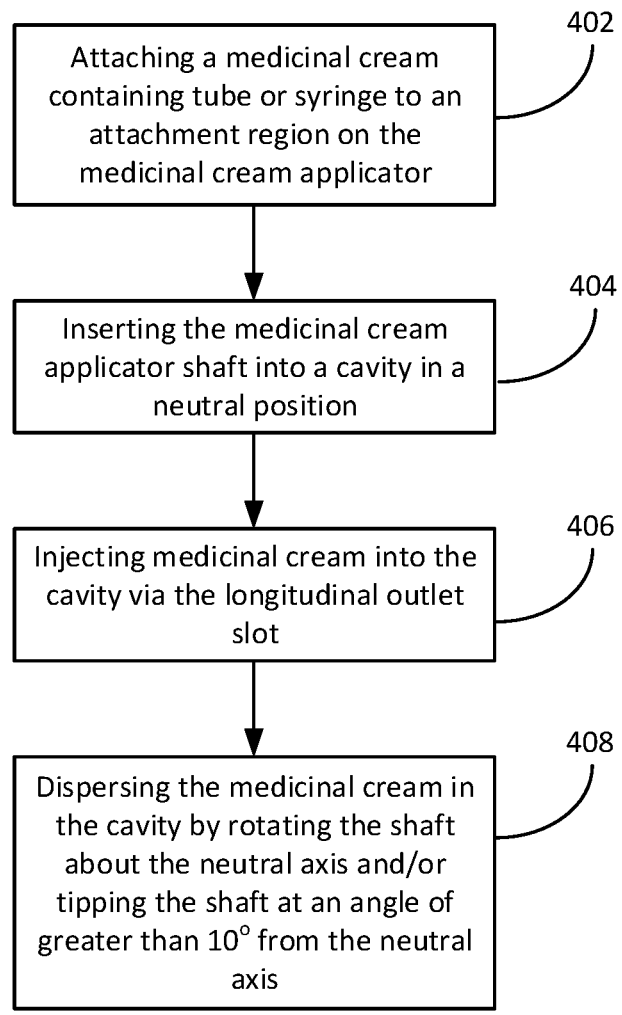
FIG. 7A is a block diagram flowchart of a method for applying medicinal cream to a human cavity consistent with embodiments of the present invention.
Figure 7B:
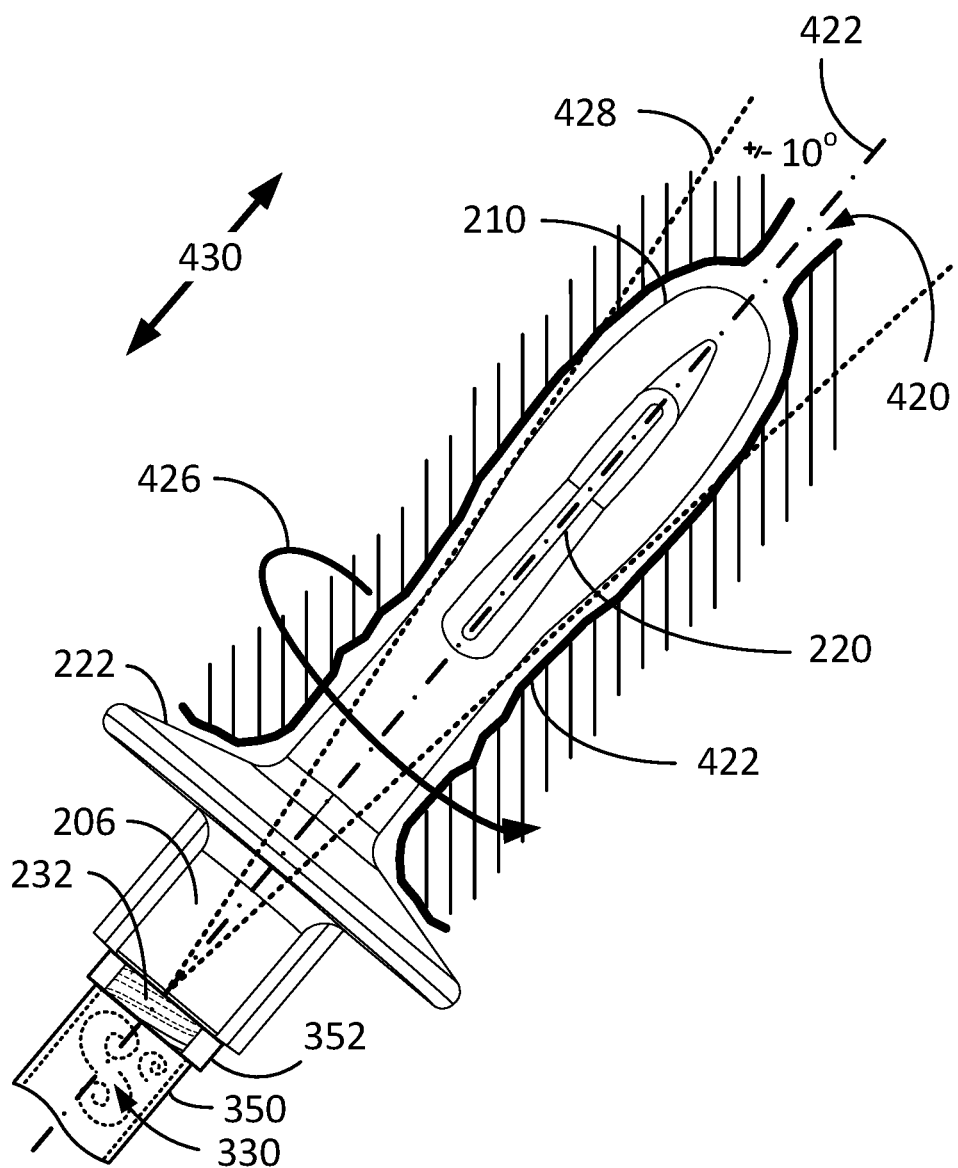
FIG. 7B is a line drawing of the medicinal applicator inserted in a human cavity.

FIG. 7A is a block diagram flowchart of a method for applying medicinal cream to a human cavity consistent with embodiments of the present invention. FIG. 7A is presented in view of FIG. 7B, which is a line drawing of the medicinal applicator 200 inserted in a human cavity 420. In step 402, the medicinal cream applicator 200 is attached to a syringe 350 containing medicinal cream 330 via the threaded post 232 that is screwed into the threaded receiving sleeve 352. When the medicinal applicator 200 is inserted into a human cavity 420 (or optionally an animal cavity), the medicinal applicator 200 positions itself in a low energy placement inside of the cavity 420, which defines a neutral axis 422, step 404. In other words, the cavity wall 424 close in around the outside of the shaft 210 to define the neutral axis 422 when the medicinal applicator 200 is devoid of any lateral force other than the cavity wall 424. When the medicinal applicator 200 is neutrally located in the cavity 420 (i.e., its natural position uninfluenced by forces other than the cavity wall 424), the neutral axis 420 aligns with the shaft axis 250 shown in FIG. 3B. With the medicinal applicator 200 inserted in the cavity 420, medicinal cream 330 is squirted through the medicinal applicator passageway 310 (of FIG. 6) and out through the longitudinal slots 220, step 406. The next step 408 is a step for dispersing the medicinal cream 350 onto the cavity wall 424 by rotating the shaft 210 about the shaft axis 250 as shown by the curved arrow 426. The shaft 210 can be rotated 426 either clockwise or counter-clockwise. The medicinal cream 330 is more effectively dispersed on the cavity wall 420 via the funneled chamber arrangement 300 of FIG. 5B. Some embodiments envision the medicinal cream 330 even more effectively dispersed on the cavity wall 420 via the shaft ribbon/flat 242 along the leading edge 270 and the trailing edge 272 (see FIG. 3B). In the present embodiment, the shaft 210 is envisioned to be rotated by a person gripping the handle 206 either when self-applying the medication or one applying the medication to another person. The medication 330 is envisioned to be further applied to the cavity wall 420 by tipping the shaft 210 at least +/−10° off the neutral axis 422, as shown by the dashed angled lines 428. When the medicinal applicator shaft 210 is tipped 10°, the shaft axis 250 aligns with the dashed lines 428. The tipping motion is envisioned to help spread the medicinal cream 330 into any crypts or nonconformities in the cavity wall 420. The medicinal cream application motion can further be augmented by moving the medicinal applicator shaft 210 in an insertion/withdrawal direction shown by the double arrow 430.

With the present description in mind, below are some examples of certain embodiments illustratively complementing some of the methods and apparatus embodiments discussed above and presented in the figures to aid the reader. Accordingly, the elements called out below are provided by example to aid in the understanding of the present invention and should not be considered limiting. The reader will appreciate that the below elements and configurations can be interchangeable within the scope and spirit of the present invention. The illustrative embodiments can include elements from the figures.

In that light, certain embodiments contemplate a medicinal applicator 200, as shown in FIG. 2A, comprising a base 205 with a medicinal cream inlet port 201 in the base 205 and a shaft 210 residing along a shaft axis 250 that extends from the base 205 to an anal applicator cap 215. As shown in FIG. 5A, a medicinal cream passageway 310 (which includes a luer taper 308, a central passageway a passageway reducer 318 and a passageway exit port 246) extends inside of the shaft 210 along the shaft axis 250 from the medicinal cream inlet port 201 to a flow directing channel 300. The medicinal cream passageway 310 joins, or is otherwise in communications with, the flow directing channel 300 at a passageway exit port 246 inside of the shaft 210. The flow directing channel 300 outwardly funnels from the passageway exit port 246 to a longitudinal outlet slot 220. The longitudinal outlet slot 220 is partially defined by a slot length 224 that is longitudinally in plane with the shaft axis 250. In other words, a plane can bisect the longitudinal outlet slot 220 and pass through the shaft axis 250. The longitudinal outlet slot 220 penetrates through an outer shaft surface 211 of the shaft 210, thereby forming communication with an outside environment interfacing the shaft outer surface 211 of the shaft 210 and the medicinal cream inlet port 201. In this way, as shown in FIG. 5C, medicinal cream 330 can enter through the medicinal cream inlet port 201 and go through the shaft 210 and out through the longitudinal outlet slot 220. The passageway exit port 246 is located between 10% and 90% of the slot length 224 from a slot proximal end 218.

Another embodiment of the medicinal applicator 200 envisions a second longitudinal outlet slot 220 that is identical to and opposing the longitudinal outlet slot 220 along the shaft 210. Still some embodiments envision a third longitudinal outlet slot 220 that is identical to the longitudinal outlet slot 220 and the second longitudinal outlet slot 220. The three longitudinal outlet slots 220 can be dispersed equally along the shaft radius at 120° apart. A fourth longitudinal outlet slot 220 is also contemplated.

The medicinal applicator 200 can further be wherein the longitudinal outlet slot 220 joins the outer shaft surface 211 by way of slot rounds 228 (fillets), wherein the longitudinal outlet slot 220 is defined at a slot round interface of the slot rounds 228. In the present medicinal applicator 200, the slot rounds 228 comprise a slot fillet taper region 244 wherein as if gets closet to the shaft proximal region 226, the slot rounds 228 widen radially along the shaft 210 while becoming shallower in depth towards the slot-round interface 227 of the longitudinal outlet slot 220. Certain other embodiments envision the slot rounds 228 being fillets that comprise a radius.

Embodiments of the medicinal applicator 200 imagine the base 205 comprising a handle 206 and a medicinal cream dispensing connector that can connect to a rube of medicinal cream or a syringe filled with medicinal cream, for example. In the embodiment shown in FIG. 6, the medicinal cream dispensing connector is a threaded post 232 that is configured to connect or screw into an internally threaded sleeve.

It is further pondered that the shaft 210 of the medicinal applicator 200 can comprise a proximal shaft region 241 that transitions into a paddle region 240. The proximal shaft region 241 can be defined by a uniform distance between the leading shaft edge 270 and a trailing shaft edge 272. The paddle region 240 possessing a larger distance between the leading shaft edge 270 and the trailing shaft edge 272, which in the embodiment shown in FIG. 4D is oblong.

In another embodiment of the medicinal applicator 200, the flow directing channel 300 can comprise a proximal slot ramp 304 that ramps from a chamber funnel inlet 245 to the slot proximal end 218 and a distal slot ramp 320 that ramps from the chamber funnel inlet 245 to a distal slot end 216. The chamber funnel inlet 245 is located at the passageway exit port 246. The proximal slot ramp 304 can be at a proximal ramp angle 306 of between 6° and 12° and the distal slot ramp 320 is at a distal ramp angle 322 between 12° and 18°. In some embodiments the proximal ramp angle 306 is approximately 9° and the distal slot ramp 320 is at a distal ramp angle 322 of approximately 15°. The longitudinal outlet slot 220 can further be defined by a slot width 274 that is essentially constant along the slot length 224 of the flow directing channel 300 comprising a flow channel width that is essentially equal to the slot width 274.

In yet another embodiment of the present inventions, as shown in FIG. 2A, an applicator 200 for deploying medicinal cream 330 can comprise a rectal/vaginal shaft 210 separated from a handle 206 via a stop plate 208. A shaft axis 250 is defined extending through the center of the handle 206 to a shaft cap 215 to where the shaft 210 terminates distally 214. A longitudinal outlet slot 220 is at least partially defined by a slot length 224 residing lengthwise in the shaft 210 between the stop plate 208 and the shaft cap 215. As shown in FIG. 5A, a passageway 310 extends inside of the shaft 210 from a receiving port 201 in the handle 206 to a passageway exit port 246 inside of the shaft 210. The passageway exit port 246 is located between 10% of a proximal end 218 of the slot length 224 and 90% of the slot length 224. The receiving port 201 is in communication with the longitudinal outlet slot 220 via the passageway exit port 246.

The applicator embodiment 200 for medicinal cream is further envisioned having the passageway exit port 246 that links the passageway 310 to a chamber funnel inlet 245, the chamber funnel inlet 245 funnels outwardly (via proximal ramps 304 and distal ramps 320) to the longitudinal outlet slot 220. This defines a funneled chamber 300. The funneled chamber 300 is further envisioned to comprise opposing parallel chamber walls 326. The applicator embodiment 200 can further comprise a second longitudinal outlet slot 220 that is identical to and opposing the longitudinal outlet slot 220 along the shaft 210 or optionally a third or fourth longitudinal outlet slot 220 dispersed along the shaft radius.

The applicator embodiment 200 for medicinal cream can further be wherein the handle 206 includes a medicinal cream dispensing connector configured to connect to a syringe 356.

Still another embodiment envisions a rectal/vaginal medicinal applicator (or simply "applicator") 200 as shown in FIG. 2A, can comprise a shaft 210 that extends from a base 205 to a distal end 214 via a stop plate 208. There are at least two longitudinal parallel outlet slots (or simply "outlet slots") 220, as shown in FIG. 5A. Each outlet slot defining a slot length 224 residing lengthwise along the shaft 210 between the stop plate 208 and the distal end 214. A passageway 310 inside of the applicator 200 communicatively links an inlet port 201 in the base 205 to a passageway exit port 246 inside of the shaft 210. Communicatively links means that the inlet port 201 is in communication with the passageway outlet port 246 so that medicinal cream can flow without obstruction there through. At least two flow directing channels 300, wherein each flow directing channel 300 funnels outwardly from the passageway exit port 246 to a corresponding one of the longitudinal outlet slots 220. The passageway exit port 246 is located between 10% and 90% of the slot length 224. The inlet port 201 is in communication with the outlet slots 220 via the passageway 310 and the flow directing channels 300.

The rectal/vaginal medicinal applicator embodiment 200 envisions the handle 206 including a medicinal cream dispensing connector 232 configured to connect to a syringe 356.

The rectal/vaginal medicinal applicator embodiment 200 imagines the shaft 210 being paddle shaped.

The rectal/vaginal medicinal applicator embodiment 200 also imagines that each of the flow directing channels 300 funnels outwardly to the corresponding longitudinal outlet slot 220 via a proximal ramp 304 and a distal slot ramp 320.

The above sample embodiments should not be considered limiting to the scope of the invention whatsoever because many more embodiments and variations of embodiments are easily conceived within the teachings, scope and spirit of the instant specification.

It is to be understood that even though numerous characteristics and advantages of various embodiments of the present invention have been set forth in the foregoing description, together with the details of the structure and function of various embodiments of the invention, this disclosure is illustrative only, and changes may be made in detail, especially in matters of structure and arrangement of parts within the principles of the present invention to the full extent indicated by the broad general meaning of the terms in which the appended claims are expressed. For example, though the proximal slot ramp 304 and distal slot ramp 320 are depicted as linear in the present embodiments other ramp shapes (e.g., curved) and other ramp angles could equally be used while still maintaining substantially the same functionality without departing from the scope and spirit of the present invention. Another example can include providing various other shaped shafts (such as a constant oblong shaped shaft or a circular shaped shaft) that meet the functionality of spreading medicinal cream in the folds of an anal canal without departing from the scope and spirit of the present invention. Yet another example can include variations of an enlarged dome shaped cap relative to the shaft diameter or other optional shaped caps within the scope and spirit of the present invention. It should be appreciated that elements of various embodiments described herein can be combined in obvious manners by a person skilled in the art that understands the content of the present specification without departing from the scope of the subject matter presented herein. Further, the term "one" is synonymous with "a", which may be a first of a plurality.

It will be clear that the present invention is well adapted to attain the ends and advantages mentioned as well as those inherent therein. While presently preferred embodiments have been described for purposes of this disclosure, numerous changes may be made which readily suggest themselves to those skilled in the art and which are encompassed in the spirit of the invention disclosed.

What is claimed is:

1. A method comprising:
   providing a shaft that extends in a longitudinal direction from a base to an anal applicator cap;
   forcing medicinal cream along a passageway between an inlet port in the base through a passageway exit port defined where the passageway terminates in the shaft, an axis passing through the center of: the shaft, the applicator cap, the inlet port, the passageway, the passageway exit port and a diversion member that is spaced away from and distally opposing the passageway exit port; and
   flowing the medicinal cream from the passageway exit port and along a distal ramp that extends to a distal slot end of a longitudinal outlet slot in the shaft, wherein the distal ramp transitions from the diversion member.

2. The method of claim 1, wherein the diversion member is conical shaped in two dimensions.

3. The method of claim 1 further comprising ejecting the medicinal cream from the longitudinal outlet slot.

4. The method of claim 1, wherein the shaft further comprising a proximal ramp that extends from the passageway exit port to a proximal slot end of the longitudinal outlet slot, wherein the proximal slot end is closer to the base than the passageway exit port.

5. The method of claim 4, wherein the passageway exit port is located between 10% and 90% of a slot length from the slot proximal end, the slot length is the distance between the slot proximal end and the slot distal end.

6. The method of claim 4 further comprising flowing the medicinal cream along the proximal ramp towards the base.

7. The method of claim 1 further comprising rotating the shaft in an anus or a vagina while dispensing the medicinal cream from the longitudinal slot.

8. The method of claim 1 further comprising ejecting the medicinal cream from a second longitudinal outlet slot that is offset 180° on the shaft from the longitudinal slot by flowing the medicinal cream along a second distal ramp and a second proximal ramp that are mirror images of the distal ramp and the proximal ramp, respectively, the second distal ramp extending from the diversion member.

9. The method of claim 1, wherein the longitudinal slot extends through a surface of the shaft and provides communication between the passageway exit port and an external environment to the shaft.

10. The method of claim 1 further comprising connecting a medicinal cream dispenser to the base prior to the forcing step.

11. A method of dispensing medicinal cream into a body cavity, the method comprising:
    forcing the medicinal cream along a passageway in an applicator between an inlet port in a base to an exit port defined where the passageway terminates in a shaft;
    defining an axis that passes through the center of: the shaft, an applicator cap, the inlet port, the passageway, the exit port and a diversion member that is spaced away from and distally opposing the exit port; and
    flowing the medicinal cream through the exit port, along a distal ramp that extends to a distal slot end of a longitudinal outlet slot in the shaft, and out from the shaft via the longitudinal slot, wherein the distal ramp transitions from the diversion member.

12. The method of claim 11, wherein the diversion member comprises an apex, which is the closest portion of the diversion member to the exit port, the diversion member having a second side that extends from the apex, the second side connects to a second distal ramp that is the mirror image of the distal ramp, the second distal ramp extending to a second longitudinal outlet slot that is the mirror image of the longitudinal outlet slot, the second longitudinal outlet slot located on an opposite side of the shaft relative to the longitudinal outlet slot.

13. The method of claim 12 further comprising diverting the medicinal cream over the diversion member second side, along the second distal ramp and out of the second longitudinal outlet slot.

14. The method of claim 11, wherein the shaft further comprising a proximal ramp that extends to a proximal slot end of the longitudinal outlet slot from the passageway exit port, the proximal slot end is closer to the base than the exit port.

15. The method of claim 11, wherein the passageway exit port is located between 10% and 90% of a slot length from the slot proximal end, the slot length is the distance between the slot proximal end and the slot distal end.

16. The method of claim 14 further comprising flowing the medicinal cream along the proximal ramp towards the base.

17. The method of claim 11 further comprising rotating the shaft in the body cavity while dispensing the medicinal cream from the longitudinal outlet slot.

18. A medicinal cream dispensing method comprising:
    moving medicinal cream through a passageway in an applicator from an inlet port in an applicator base through an exit port where the passageway terminates in an applicator shaft;
    from the exit port, diverting the medicinal cream over a diversion member, along a distal ramp that extends from the diversion member to a longitudinal outlet slot, and out from the applicator shaft via the longitudinal outlet slot,
    the diversion member comprising an apex that is spaced away from and opposes the exit port, the apex and the exit port are along an axis defined as extending through the middle of the applicator shaft.

19. The medicinal cream dispensing method of claim 18 further comprising diverting the medicinal cream over an opposite side of the diversion member, along a second distal ramp that is the mirror image of the distal ramp, the second distal ramp extending from the opposite side of the diversion member to a second longitudinal outlet slot that is the mirror image of the longitudinal outlet slot, the second longitudinal outlet slot located on the opposite side of the applicator shaft.

20. The medicinal cream dispensing method of claim 18, wherein the shaft further comprising a proximal ramp that extends to a proximal slot end of the longitudinal outlet slot from the passageway exit port, the proximal slot end is closer to the base than the exit port.

\* \* \* \* \*